United States Patent
Burns

(10) Patent No.: US 7,232,831 B2
(45) Date of Patent: Jun. 19, 2007

(54) TETRAHYDRO-β-CARBOLINE COMPOUNDS AND USE THEREOF

(75) Inventor: Mark R. Burns, Shoreline, WA (US)

(73) Assignee: MediQuest Therapeutics, Inc., Bothell, WA (US)

( * ) Notice: Subject to any disclaimer, the term of this patent is extended or adjusted under 35 U.S.C. 154(b) by 138 days.

(21) Appl. No.: 10/805,222

(22) Filed: Mar. 22, 2004

(65) Prior Publication Data

US 2005/0209264 A1    Sep. 22, 2005

(51) Int. Cl.
    A61K 31/44    (2006.01)
    C07D 471/04   (2006.01)

(52) U.S. Cl. .................... 514/292; 546/81

(58) Field of Classification Search ............. 546/81; 514/292

See application file for complete search history.

(56) References Cited

U.S. PATENT DOCUMENTS 5,162,336 A * 11/1992 Molino et al. ............... 514/292

FOREIGN PATENT DOCUMENTS

WO    WO 9200295    * 1/1992

OTHER PUBLICATIONS

Tetrahydro-β-carbolines, Potential Neuroactive Alkaloids, in Chocolate and Cocoa by Tomas Herraiz, J. Agric. Food Chem. 2000, 48, pp. 4900-4904.
Glutamate Receptors in the Mammalian Central Nervous System, by Seiji Ozawa et al., Progress in Neurobiology vol. 54, pp. 581-618, 1998.
Glutamate Neurotoxicity and Diseases of the Nervous System, by Dennis Choi, Neuron, vol. 1, pp. 623-634, Oct. 1988.
NMDA receptors as targets for drug action in neuropathic pain, by Chris Parsons, European Journal of Pharmacology 429, 2001, pp. 71-78.
Synergistic effect of uncompetitive NMDA receptor antagonists and antidepressant drugs in the forced swimming test in rats, by Zofia Rogoz et al., Neuropharmacology 42, 2002, pp. 1024-1030.
Modulation of the NMDA Receptor by Polyamines, by Keith Williams, et al., Life Sciences, vol. 48, pp. 469-498, 1991.
Characterization of the Effects of Polyamines on [$^{125}$I] MK-801 Binding to Recombinant N-Methyl-D-Aspartate Receptors, by Terre Sharma et al., The Journal of Pharmacology and Experimental Therapeutics, 1999, pp. 1041-1047.
Endogenous indoles as novel polyamine site ligands as the N-methyl-D-aspartate receptor complex, by David Worthen et al., Brain Research 890 2001, pp. 343-346.
$N^1$-Dansyl-Spermine and $N^1$-(n-Octanesulfonyl)-Spermine, Novel Glutamate Receptor Antagonists: Block and Permeation of N-Methyl-D-Aspartate Receptors, by James Chao et al., Molecular Pharmacology, pp. 861-871 1997.
Functional antagonists at the NMDA receptor complex exhibit antidepressant actions, by Ramon Trullas et al., European Journal of Pharmacology 185 1990, pp. 1-10.
Potential Antidepressive Properties of Amantadine, Memantine and Bifemelane, Elzbieta Moryl et al., Pharmacology & Toxicology 1993, 72, pp. 394-397.
The N-methyl-D-aspartate receptor channel blockers memantine, MRZ 2/579 and other amino-alkyl-cyclohexanes antagonise 5-HT$_3$ receptor currents in cultured HEK-293 and N1E-115 cell systems in a non-competitive manner, by G. Rammes et al., Neuroscience Letters 306 2001, pp. 81-84.
Memantine is a clinically well tolerated N-methyl-D-aspartate (NMDA) receptor antagonist-a review of preclinical data, by C.G. Parsons et al., Neuropharmacology, 38, 1999, pp. 735-767.
NMDA Receptor Antagonists and Antidepressant Drugs, by J. Maj, Pharmacological Research, vol. 25, Supplement 2, 1992.
Anticonvulsant effects of eliprodil alone or combined with the glycine$_a$ receptor antagonist L-701, 324 or the competitive NMDA antagonist CGP 40116 in the amygdala kindling model in rats, by Piotr Wlaz et al., Neurophamacology 38, 1999, pp. 243-251.
Synthesis and Resolution of Racemic Eliprodil and Evaluation of the Enantiomers of Eliprodil as NMDA Receptor Antagonists, by Jorg Pabel et al., Bioorganic & Medicinal Chemistry Letters, 10, 2000, pp. 1377-1380.

(Continued)

Primary Examiner—Rita Desai
(74) Attorney, Agent, or Firm—Connolly, Bove, Lodge & Hutz, LLP

(57) ABSTRACT

Tetrahydro-β-carboline compounds represented by the following formulae:

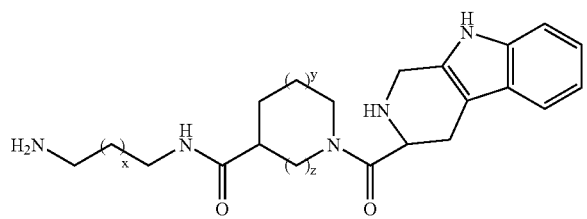

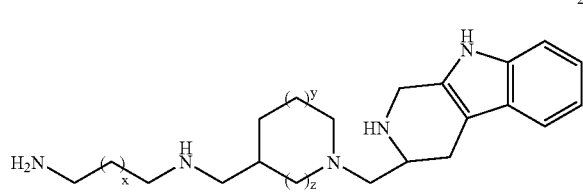

wherein x, y and z are each independently an integer of 0 to 4 and R is selected from the group consisting of H, alkyl, aryl and heterocyclic moiety wherein the alkyl, aryl and heterocyclic moiety are optionally substituted with a member selected from the group consisting of halogen, alkoxy and trifluoromethyl; pharmaceutically acceptable salts thereof and prodrugs thereof are provided. The compounds are useful for treating neurological diseases.

11 Claims, 3 Drawing Sheets

OTHER PUBLICATIONS

Affinities of 5-HT Uptake Inhibitors for 5-Ht3 Receptors in Both Binding and Functional Studies, GJ Kilpatrick et al., Brit J. Pharmacol. 1989 98 (suppl.) #17 pp. 859.

The interaction of antidepressant drugs with central and peripheral (enteric) $5-HT_3$ and $5-HT_4$ receptors, by A. Lucchelli et al., British Journal of Pharmacology 1995, 114, pp. 1017-1025.

Higher-End Serotonin Receptors: $5-HT_5$, $5_6$, and $5-HT_7$, by Richard Glennon, Journal of Medicinal Chemistry, 2003, vol. 46, No. 14, pp. 2795-2812.

Molecular, pharmacological and functional diversity of 5-HT receptors, by Daniel Hoyer et al., Pharmacology, Biochemistry and Behavior 71, 2002, pp. 533-554.

Multiple MPEP administrations evoke anxiolytic- and antidepressant-like effects in rats, by A. Pilc et al., Neuropharmacology, 43, 2002, pp. 181-187.

Antidepressant and anxiolytic-like effects in mice lacking the group III metabotropic glutamate receptor mGluR7, by John Cryan et al., European Journal of Neuroscience, vol. 17, pp. 2409-2417, 2003.

Solid Phase Synthesis of Heterocyclic Compounds from Linear Peptides: Cyclic Ureas and Thioureas, by Adel Nefzi et al., Tetrahderon Letters, vol. 38, No. 6, pp. 931-934, 1997.

Antidepressants for the new millennium by Phil Skolnick, European Journal of Pharmacology 375, 1999, pp. 31-40.

Mild Oxidative Cleavage of Borane-Amine Adducts from Amide Reductions: Efficient Solution-and Solid Phase Synthesis of N-Alkylamino Acids and Chiral Oligoamines, by Dennis Hall et al., J. Org. Chem. 1999, 64, pp. 698-699.

Behavioural Despair in Rats: A New Model Sensitive to Antidepressant Treatments, by Roger Porsolt et al., European Journal of Pharmacology, 47 (1978), pp. 379-391.

Anxiogenic Effects of Methyl-β-Carboline-3-Carboxylate in a Light/Dark Choice Situation, by Catherine Belzung et al., Pharmacology Biochemistry & Behavior, vol. 28, pp. 29-33, 1987.

* cited by examiner

# TETRAHYDRO-β-CARBOLINE COMPOUNDS AND USE THEREOF

TECHNICAL FIELD

The present invention relates to tetrahydro-β-carboline compounds and more particularly to tetrahydro-β-carboline bisamide compounds and tetrahydro-β-carboline tetraamine compounds. The compounds of the present invention are especially useful for treating neurological diseases, such as, but not limited to, depression and anxiety.

BACKGROUND OF THE INVENTION

The impact of chemotherapeutic intervention in psychiatric disorders in the last century has been profound. Dramatic scientific progress towards understanding the basic biochemical mechanisms of action of these agents has been made. Despite these advances, vast areas of understanding still remain to be uncovered. Insight into the outcomes from the summation of numerous interactions with various receptors and receptor subtypes promises to lead to the invention of powerful neuroactive medicines.

A variety of simple tetrahydro-β-carboline compounds have been found in natural sources and some of these compounds have been associated with neurological activities. Rommelspacher, H. et. al. Beta-carbolines and tetrahydroisoquinolines: detection and function in mammals. Planta Med. 1991, 57(7), S85-92. Produced naturally via a Pictet-Spengler condensation reaction between indoleamines and aldehydes, these molecules have been observed in mammalian tissues and their association with food sources has led to speculation about their potential biological effects in chocolate and alcohol cravings. Herraiz, T. Tetrahydro-b-carbolines, potential neuroactive alkaloids, in chocolate and cocoa. J. Agric. Food Chem. 2000, 48, 4900-4904; Adell, A; Myers, R. D. Increased alcohol intake in low alcohol drinking rats after chronic infusion of the b-carboline Harman into the hippocampus. Pharmacol. Biochem. Behav. 1994, 49, 949-953.

The N-methyl-D-aspartate (NMDA) receptors are multisubunit, ligand-gated ion channels with multiple regulatory sites around the central ion channel. These receptors gate $Na^+$, $Ca^{2+}$ and $K^+$ ions into and out of cells. They are widely distributed in the central nervous system. NMDA receptors are activated by glutamate resulting in cation flux and cell depolarization. See Ozawa, et al., Glutamate receptors in the mammalian central nervous system. Prog. Neurobiol. 1998, 54, 581-618.

NMDA activation is believed to play an important role in learning and memory. However, over-activation can result in excitotoxic neuronal damage. For this reason antagonists of NMDA activation have been proposed as therapeutics for Alzheimer's disease and Parkinson's disease. See Choi, Glutamate neurotoxicity and diseases of the nervous system. Neuron 1988, 8, 623-634.

NMDA antagonists have also shown utility as possible therapeutics in pain, (see Parsons, NMDA receptors as targets for drug action in neuropathic pain. Eur. J. Pharmacol. 2001, 429, 71-78), depression and anxiety (see Rogoz, et al. Synergistic effect of uncompetitive NMDA receptor antagonists and antidepressant drugs in the forced swimming test in rates. Neuropharmacol. 2002, 42, 1024-1030).

Mutiple polyamine binding sites on the N-methyl-D-aspartate (NMDA) receptor-channel have the ability to modulate NMDA activity. See Williams, et al. Minireview. Modulation of the NMDA receptor by polyamines. Life Sciences 1991, 48(6), 469-498; and Sharma, et al. Characterization of the effects of polyamines on [125]MK-801 binding to recombinant N-methyl-D-aspartate receptors. J. Pharmacol. Exper. Therap. 1999, 289(2), 1041-1047.

Antagonism at the polyamine binding sites may prevent the NMDA receptor from being over-stimulated. See Worthen, et al. Endogenous indoles as novel polyamine site ligands at the N-methyl-D-aspartate receptor complex. Brain Res. 2001, 890, 343-346.

A major advantage in using polyamine site-specific NMDA antagonists lies in their ability to modulate without completely blocking NMDA receptor activation. Polyamines and polyamine analogs also have effect on non-NMDA glutamate receptors. See Chao, et al. $N^{1-}$ dansyl-spermine and $N^1$-(n-octanesulfonyl)-spermine, novel glutamate receptor antagonists: Block and permeation of N-methyl-D-aspartate receptors. Molec. Pharmacol. 1997, 51, 861-871.

NMDA antagonists, other than polyamine analogs, have also been proposed for possible therapeutic application in depression and anxiety. See Trullas, et al. Functional antagonists of the NMDA receptor comples exhibit antidepressant action. Eu. J Pharmacol. 1990, 185, 1-10; Moryl, et al. Potential antidepressive properties of amantadine, memantine and bifemelane. Pharma. and Tox. 1993, 72, 394-397; and Skolnick, Antidepressants for the new millennium. Eur. J Pharmacol. 1999, 375, 31-40.

The NMDA receptor antagonist memantine has been shown to antagonize the 5-$HT_3$ receptor and that may account for its antidepressant effects. See Rammes, et al. The NMDA receptor channel blockers memantine, neramexane and other amino-alkyl-cyclohexanes also antagonize 5-$HT_3$ receptor currents in HEK-293 and N1E-115 cells in a uncompetitive manner. Neuroscience Lett. 2001, 306, 81-84; and Parsons, et al. Memantine is a clinically well tolerated N-methyl-D-aspartate (NMDA) receptor antagonist—a review of preclinical data. Neuropharmacology 1999, 38, 735-767.

Other competitive antagonists of NMDA receptors, e.g. CGP 37849 or AP-7, also show anti-depression effects in the forced swimming test in rates. See Maj. NMDA receptor antagonists and antidepressant drugs. Pharmacol Res. 1992, 25, R1.

NMDA antagonists used in conjunction with antidepressants have shown synergistic anti-depressant effects and may be particularly useful for drug-resistant depression. See Rogoz et al., supra.

Improved effects may be seen with other combination therapies such as antagonists at the polyamine and glycine sites for treating therapy-resistant complex partial seizures. See Wlax et al. Anticonvulsant effects of eliprodil alone or combined with the glycine$_B$ receptor antagonist L-701, 324 or the competitive NMDA antagonist CGP 40116 in the amygdala kindling model in rats. Neuropharmaco. 1999, 38, 243-251.

Improvements in CNS drugs may involve identifying the active stereochemical isomer, as in the case of eliprodil, a ligand selective for the NR2B subunit of the NMDA receptor. See Pabel, et al. Synthesis and resolution of racemic eliprodil and evaluation of the enantiomers of eliprodil as NMDA receptor antagonists. Bioorganic & Med. Chem. Lett. 2000, 10, 1377-1380.

In addition, antidepressants may work through interactions with various 5-HT receptors. See Kilpatrick, et al. Affinities of 5-HT uptake inhibitors for 5-HT3 receptors in both binding and functional studies. Brit J. Pharmacol. 1989, 98 (Suppl.): 859; Lucchelli, et al. The interaction of antidepressant drugs with central and peripheral (enteric) 5-HT3 and 5-HT4 receptors. *Brit J. Pharmacol.* 1995, 114, 1017-1025; and Glennon, Higher-end serotonin receptors: 5-HT$_5$, 5-HT$_6$, and 5-HT$_7$. *J. Med. Chem.* 2003, 46, 2795-2812.

Serotonin (5-HT: 5 hydroxytryptamine) is a small molecule neurotransmitter whose actions and concentrations are regulated through receptors and cellular transporters. See Hoyer, et al. Molecular, pharmacological and functional diversity of 5-HT receptors. *Pharmacology, Biochem. and Behavior* 2002, 71, 533-554.

Serotonin, acting through its various receptors, is implicated in numerous disease states: depression, anxiety, schizophrenia, migraines, eating disorders, panic, hypertension, vomiting, social phobias, obsessive-compulsive disorders, pulmonary hypertension, and irritable bowel syndrome. See Hoyer, et al. supra. The 5-HT transporter is the target for selective serontonin reuptake inhibitors, an important class of antidepressants. There are seven families of receptors (5-HT$_{1-7}$) based on their structure, operation and transduction. Furthermore, there are numerous subtypes of each family of 5-HT receptor. One of the families, 5-HT$_3$, is a ligand-gated ion channel while the others are G-protein-systems, the gut cardiovascular system and blood. Receptor subtypes show specific localization patterns.

Furthermore, glutamate neurotransmission has been implicated in anxiety and depression. Antagonists of group I metabotropic glutamate receptors (mGluR), group II MGluR[22] and group III mGluR[23] have potential use against depression and anxiety. See Pilc, et al. Multiple MPEP administrations evoke anxiolytic-and antidepressant-like effects in rats. *Neuropharma.* 2002, 43(2), 181-187; Chjnacka-Wojcik, et al. Glutamate receptor ligands as anxiolytics. *Curr Opin Investig Drugs.* 2001, 2(8), 1112-1119; and Cryan, et al. Antidepressant and anxiolytic-like effects in mice lacking the group III metabotropic glutamate receptor MGluR[7]. *Eur J Neurosci.* 2003, 17(11), 2409-2417; respectively.

Notwithstanding the above providing new treatments for neurological diseases would be desirable.

BRIEF SUMMARY OF THE INVENTION

The present invention relates to tetrahydro-β-carboline compounds represented by the following formulae:

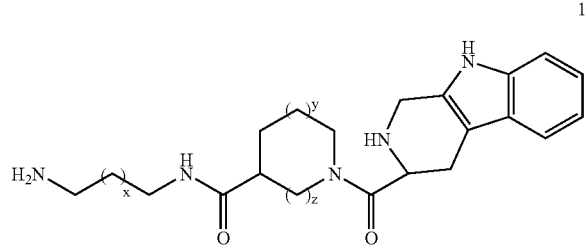

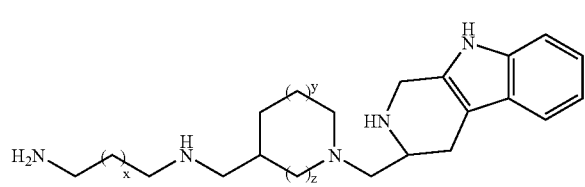

wherein x, y and z are each independently an integer of 0 to 4, and R is selected from the group consisting of H, alkyl, and aryl and heterocyclic moiety wherein the alkyl, aryl and heterocylic moiety are optionally substituted with a member selected from the group consisting of halogen, alkoxy and trifluoromethyl; pharmaceutically acceptable salts thereof and prodrugs thereof.

The present invention also relates to pharmaceutical compositions containing at least one of the above disclosed compounds as an active ingredient.

A further aspect of the present invention relates to treating a neurological disease by administering to a patient suffering from a neurological disease, an effective neurological treatment amount of at least one of the above disclosed tetrahydro-β-carboline compounds.

BEST AND VARIOUS MODES FOR CARRYING OUT INVENTION

Figure 1:
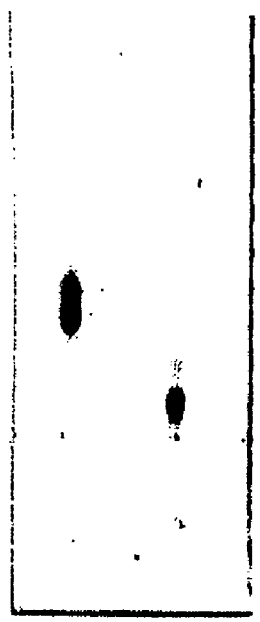
FIG. 1 are TLC analysis of tetrahydro-β-carboline compounds of the present invention.

The tetrahydro-β-carboline compounds of the present invention are represented by the following formulae:

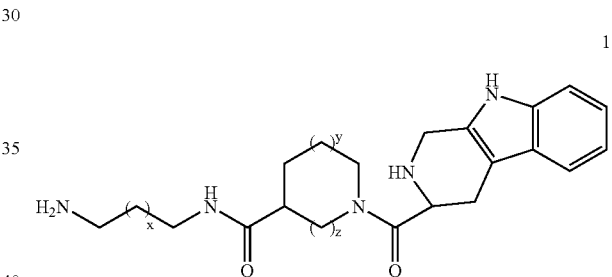

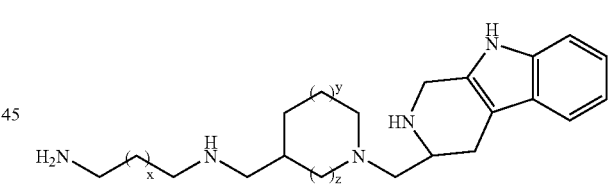

wherein x, y and z are each independently an integer of 0 to 4, and R is selected from the group consisting of H, alkyl, aryl and heterocyclic moiety wherein the alkyl, aryl and heterocyclic moiety are optionally substituted with a member selected from the group consisting of halogen, alkoxy and trifluoromethyl.

The present invention also provides for the free base or acid forms, as well as salts thereof, of the tetrahydro-β-carboline compounds described herein. The invention also includes the optical isomers of the disclosed tetrahydro-β-carboline compounds. In a further aspect of the invention, mixtures of enantiomers and/or diastereoisomers, resulting from a single preparative step, combination, or interconversion are encompassed.

The invention also provides for the prodrug forms of the above described tetrahydro-β-carboline compounds, wherein the prodrug is metabolized in vivo to produce a tetrahydro-β-carboline compound as set forth above. Indeed, some of the above described tetrahydro-β-carboline compounds may be a prodrug for another compound.

Listed below are definitions of various terms used to describe this invention. These definitions apply to the terms as they are used throughout this specification, unless otherwise limited in specific instances, either individually or as part of a larger group.

The term "aryl" refers to monocyclic or multiring aromatic hydrocarbon groups typically containing 6 to 14 carbon atoms in the ring portion, such as phenyl, 2-naphthyl, 1-naphthyl, 4-biphenyl, 3-biphenyl, 2-biphenyl, and diphenyl groups, each of which may be substituted.

The term "saturated aliphatic" refers to straight or branched chain unsubstituted hydrocarbon groups typically having 1 to 20 carbon atoms, more typically 1 to 8 carbon atoms. The expression "lower alkyl" refers to unsubstituted alkyl groups of 1 to 4 carbon atoms.

Examples of suitable saturated aliphatic or alkyl groups include methyl, ethyl and propyl. Examples of branched alkyl groups include isopropyl and t-butyl.

The term "halogen" or "halo" refers to fluorine, chlorine, bromine and iodine.

The term "heterocyclo" refers to saturated or unsaturated, single or multiringed groups.

Examples of multiring aromatic (unsaturated) heterocycle groups are 2-quinolinyl, 3-quinolinyl, 5-quinolinyl, 6-quinolinyl, 7-quinolinyl, 1-isoquinolinyl, 3-isoquinolinyl, 6-isoquinolinyl, 7-isoquinolinyl, 3-cinnolyl, 6-cinnolyl, 7-cinnolyl, 2-quinazolinyl, 4-quinazolinyl, 6-quinazolinyl, 7-quinazolinyl, 2-quinoxalinyl, 5-quinoxalinyl, 6-quinoxalinyl, 1-phthalaonyl, 6-phthalazinyl, 1-5-naphthyridin-2-yl, 1,5-naphthyridin-3-yl, 1,6-naphthyridin-3-yl, 1,6-naphthyridin-7-yl, 1,7-naphthyridin-3-yl, 1,7-naphthyridin-6-yl, 1,8-naphthyrdin-3-yl, 2,6-naphthyridin-6-yl, 2,7-naphthyridin-3-yl, indolyl, 1H-indazolyl, purinyl and pteridinyl.

Examples of single ring heterocycle groups are pyrrolyl, pyranyl, oxazolyl, thiazoyl, thiophenyl, furanyl, imidazolyl, pyrazolyl, pyridinyl, pyrazinyl, pyrimidinyl, 4-pyrimidinyl, 3-pyrimidinyl and 2-pyrimidinyl, pyridazinyl, isothiazolyl and isoxazolyl.

Examples of saturated heterocycle groups are pyrrolidinyl, imidazolidinyl, pyrazolidinyl, piperidinyl, piperazinyl, and morpholinyl.

The heterocycle groups contain N, O and/or S and typically contain 5 to 10 atoms in the ring(s), and typically contain 1, 2 or 3 heteroatoms (e.g. —N, O and S) in the ring.

The alkoxy groups typically have 1-8 carbon atoms and more typically 1-4 carbon atoms. Examples of suitable alkoxy groups are methoxy, ethoxy, and propoxy.

Prodrug forms of the compounds bearing various nitrogen functions (amino, hydroxyamino, hydrazino, guanidino, amidino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined above.

Carboxamides, —NHC(O)R
Carbamates, —NHC(O)OR
(Acyloxy)alkyl Carbamates, NHC(O)OROC(O)R
Enamines, —NHCR(=CHCRO$_2$R) or —NHCR(=CHCRONR$_2$)
Schiff Bases, —N=CR$_2$
Mannich Bases (from carboximide compounds), RCONHCH$_2$NR$_2$ Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the invention.

Prodrug forms of carboxyl-bearing compounds of the invention include esters (—CO$_2$R) where the R group corresponds to any alcohol whose release in the body through enzymatic or hydrolytic processes would be at pharmaceutically acceptable levels.

Another prodrug derived from a carboxylic acid form of the invention may be a quaternary salt type

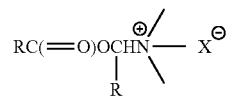

III.

of structure described by Bodor et al., J. Med. Chem. 1980, 23, 469.

It is of course understood that the compounds of the present invention relate to all optical isomers and stereoisomers at the various possible atoms of the molecule.

The compounds of this invention form acid and base addition salts with a wide variety of organic and inorganic acids and bases and includes the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphayte, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

The preferred compounds of the present invention are represented by the following formulae:
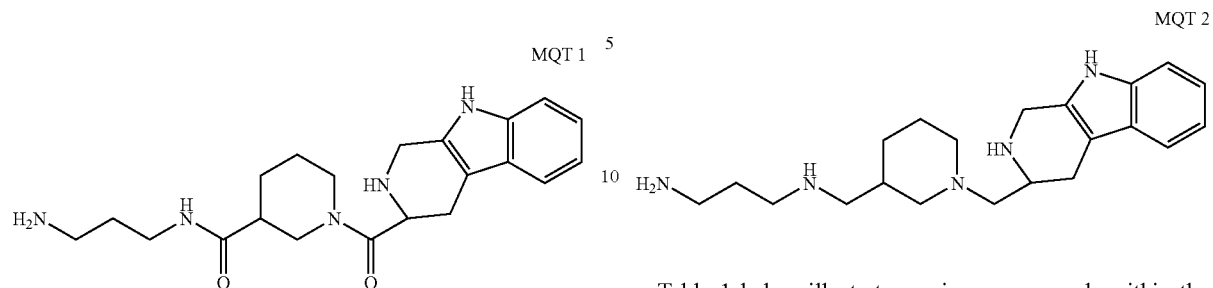
Table 1 below illustrates various compounds within the scope of the present invention that have been synthesized.
TABLE 1
TETRAHYDRO-β-CARBOLINE COMPOUNDS
| MQT # | Structure | Molecular Weight |
|---|---|---|
| 1 | 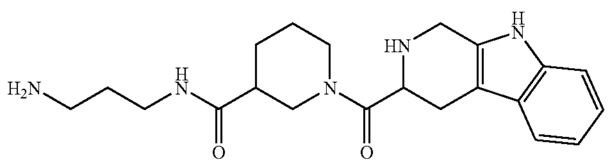 | 383.5 |
| 2 | 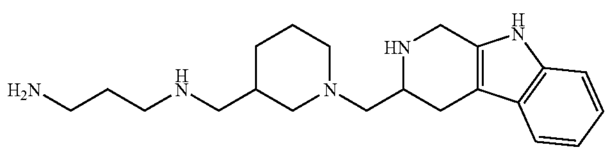 | 355.5 |
| 10 | 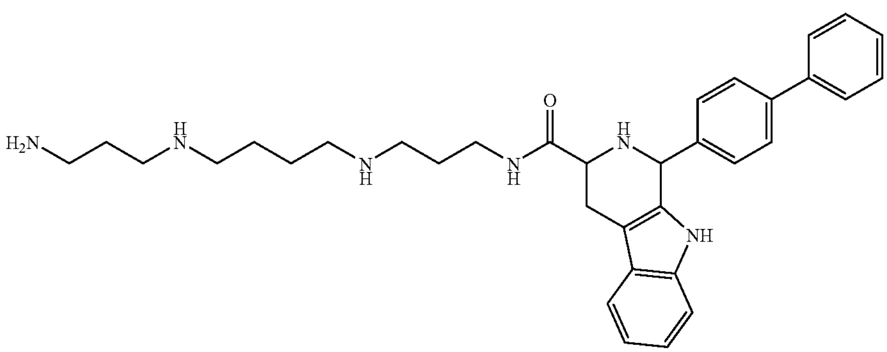 | 552.8 |
| 11 | 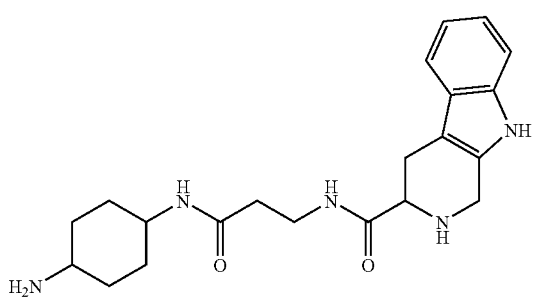 | 383.5 |

TABLE 1-continued

TETRAHYDRO-β-CARBOLINE COMPOUNDS

| MQT # | Structure | Molecular Weight |
|---|---|---|
| 12 | 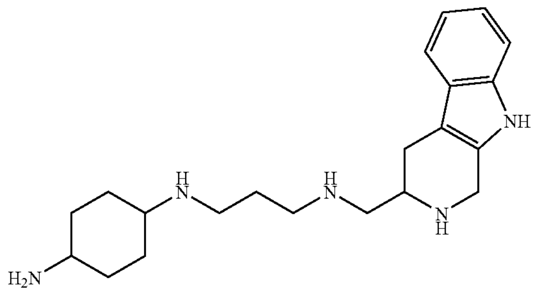 | 355.5 |
| 13 | 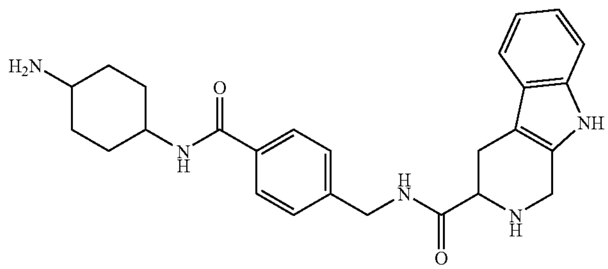 | 445.6 |
| 14 | 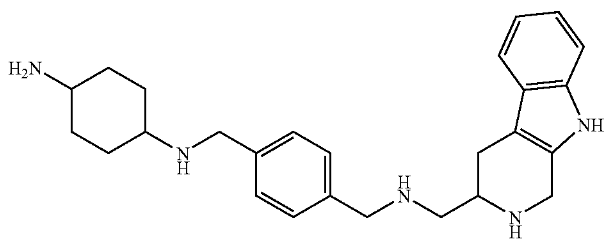 | 417.6 |
| 15 | 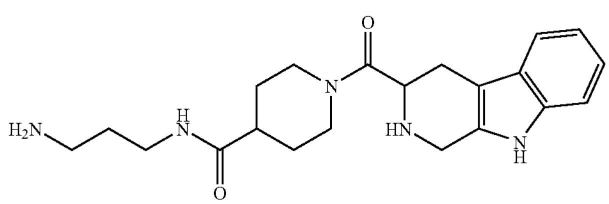 | 383.5 |
| 16 | 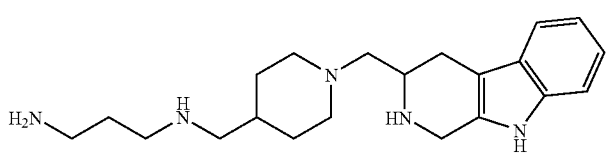 | 355.5 |
| 17 | 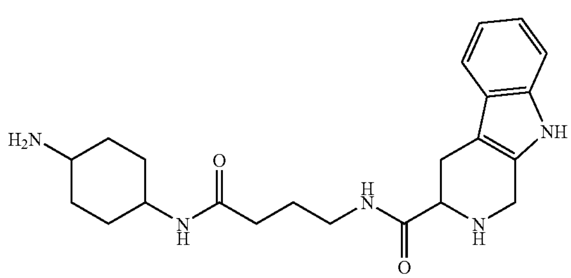 | 397.5 |

TABLE 1-continued

TETRAHYDRO-β-CARBOLINE COMPOUNDS

| MQT # | Structure | Molecular Weight |
|---|---|---|
| 18 | 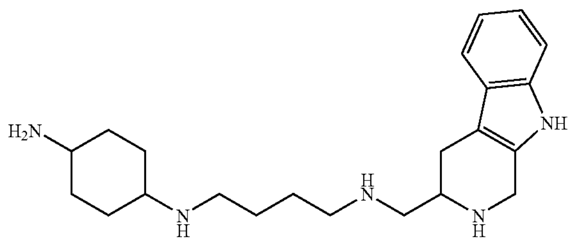 | 369.6 |
| 19 | 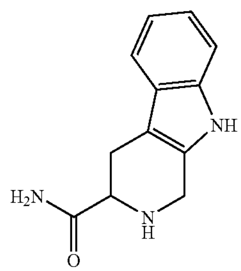 | 215.3 |
| 20 | 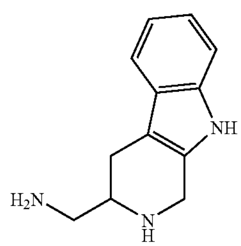 | 201.3 |
| 21 | 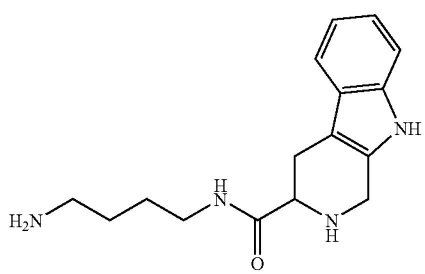 | 286.4 |
| 22 | 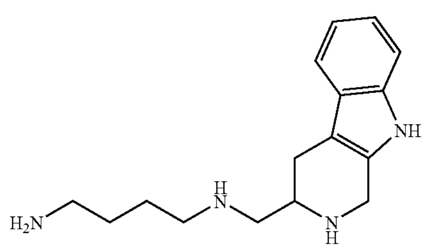 | 272.4 |

TABLE 1-continued

TETRAHYDRO-β-CARBOLINE COMPOUNDS

| MQT # | Structure | Molecular Weight |
|---|---|---|
| 23 | | 419.5 |
| 24 | | 391.6 |
| 25 | | 397.5 |
| 26 | | 369.6 |
| 27 | | 431.5 |

TABLE 1-continued

TETRAHYDRO-β-CARBOLINE COMPOUNDS

| MQT # | Structure | Molecular Weight |
|---|---|---|
| 28 | | 403.6 |
| 29 | | 326.4 |
| 30 | | 312.5 |
| 31 | | 320.4 |
| 32 | | 306.4 |

Compounds of the present invention can be fabricated by solid-phase synthesis (Scheme 1).

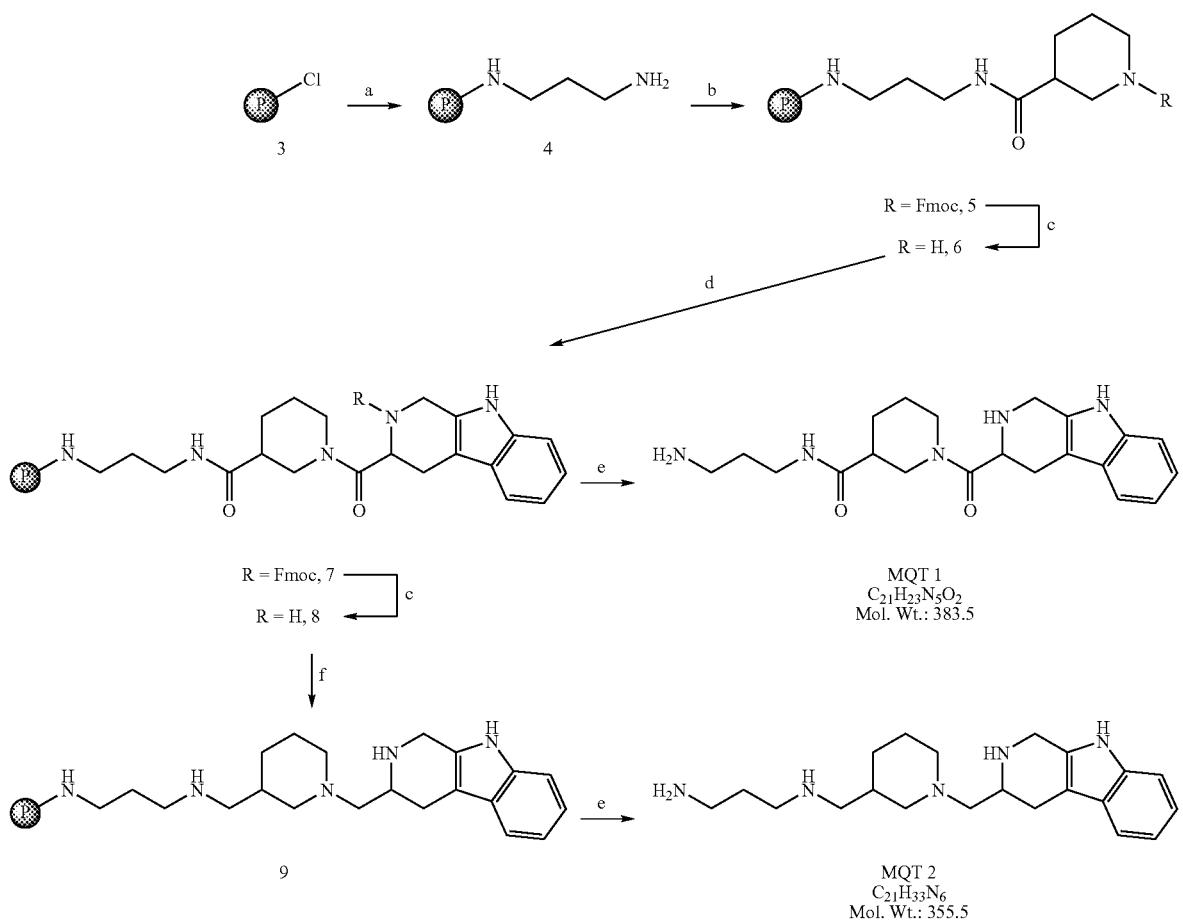

Scheme 1
Synthesis of MQT 1 and MQT 2[a].

[a]Conditions and reagents:
a  i. 3-aminopropanol, CH$_2$Cl$_2$,
   ii. PPh$_3$, phthalimide, DIAD, CH$_2$Cl$_2$,
   iii. NH$_2$NH$_2$ H$_2$O, EtOH;
b  (R,S)-Fmoc-nipecotic acid, HBTU, HOBt, $^i$Pr$_2$Net, DMF;
c  20% piperidine in DMF;
d  Fmoc-D-1,2,3,4-tetrahydronorharman-3-carboxylic acid, HBTU, HOBt, $^i$Pr$_2$Net, DMF;
e  CH$_2$Cl$_2$/TFA/$^i$Pr$_3$SiH 48:48:4;
f  i. BH$_3$, THF, B(OCH$_3$)$_3$, B(OH)$_3$, reflux,
   ii. Piperidine, reflux.

The solid-phase bis-amide compounds of the present invention can be reduced to their fully reduced polyamine counterparts by known techniques. See Nefzi, et al. Tetrahedron Lett. 1997, 38, 931; and Hall, et al. Mild oxidative cleavage of borane-amine adducts from amide reductions: efficient solution- and solid-phase synthesis of N-alkylamino acids and chiral oligioamines. *J. Org. Chem.* 1999, 64, 698–699.

In order to facilitate a further understanding of the present invention, reference is made below to the preparation of MQT 1 and MQT 2 as illustrative of the compounds of the present invention.

In particular, MQT 1 and MQT 2 are produced by a solid-phase synthetic method shown below scheme. Trityl chloride resin is treated with 3-amino-1-propanol in CH$_2$Cl$_2$ to give the amine-substituted resin with an alcohol exposed for the next reaction. Conversion of the alcohol to an amine function involves the use of standard Mitsunobu conditions followed by hydrazine-mediated hydrolysis of the phthalimide grouping. This generates the amine function ready for coupling with an FMOC-protected amino acid such as FMOC-nipecotic acid. By using the HBTU-based amide coupling conditions this solid-phase intermediate is generated. FMOC group cleavage gives the next free amino function ready for coupling with the next amino acid with 1,2,3,4-tetrahydronorharmane-3-carboxylic acid as an example. The loading efficiency can be measured following these two steps by measurement of the amount of UV chromophore produced by cleavage of the FMOC group from a measured amount of solid-phase resin. Generally, loading efficiencies of 85 to 95% are measured at this point based on the degree of loading specified by the resin manufacturer.

Following FMOC protecting group cleavage from the entire portion of resin it can be cleaved directly to provide the diamide MQT 1 or reacted under exhaustive reduction conditions using borane at 65° C. to give the solid phase precursor for the polyamine MQT 2. In the event, a high 89% yield of diamide MQT 1 is obtained by cleavage through the use of 80:18:2 $CH_2Cl_2/TFA/^iPr_3SiH$. Although this crude material had moderate purity by the analytical methods of thin layer chromatography and LC/MS, it is generally purified by the use of column chromatography over silica gel. Overall a yield of 65% can be obtained. This material has high purity as shown in FIGS. 1 and 2 by TLC and LC/MS methods. As shown in FIG. 1, the diastereomers of MQT 1 can be separated by this solvent system. These two diastereomers have been separated by column chromatography.

Reference to FIG. 1 shows the TLC analysis of MQT 1 on the left and MQT 2 on the right. The TLC analysis is carried out by eluting the TLC plate twice by 48/48/4 $CHCl_3/MeOH$/concd $NH_4OH$. Spots are detected by ninhydrin staining and heating. The plate is scanned electronically using a standard scanner and computer system.

Figure 2A:
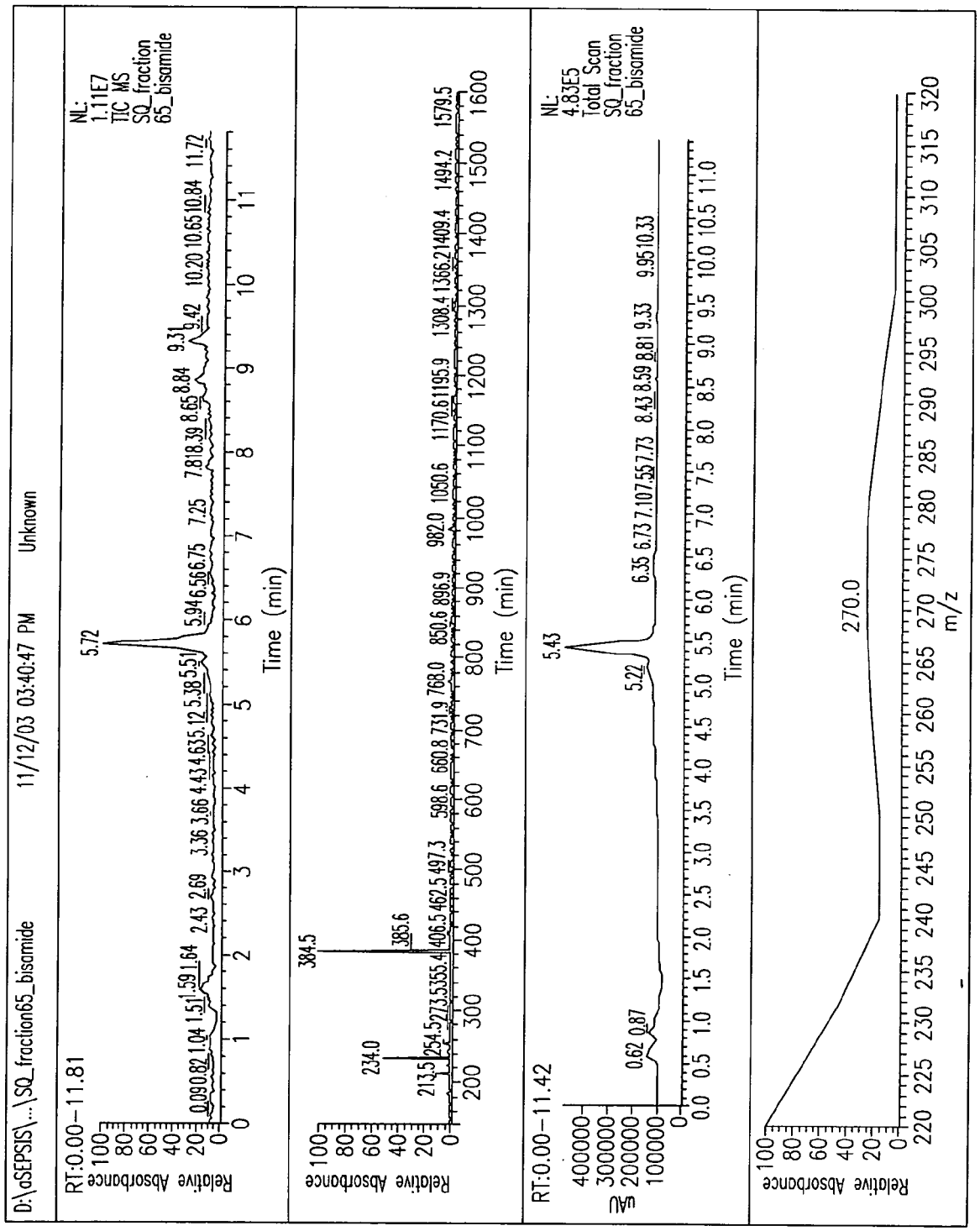
FIGS. 2A and 2B are LC/MS analysis of tetrahydro-β-carboline compound of the present invention.
Figure 2B:
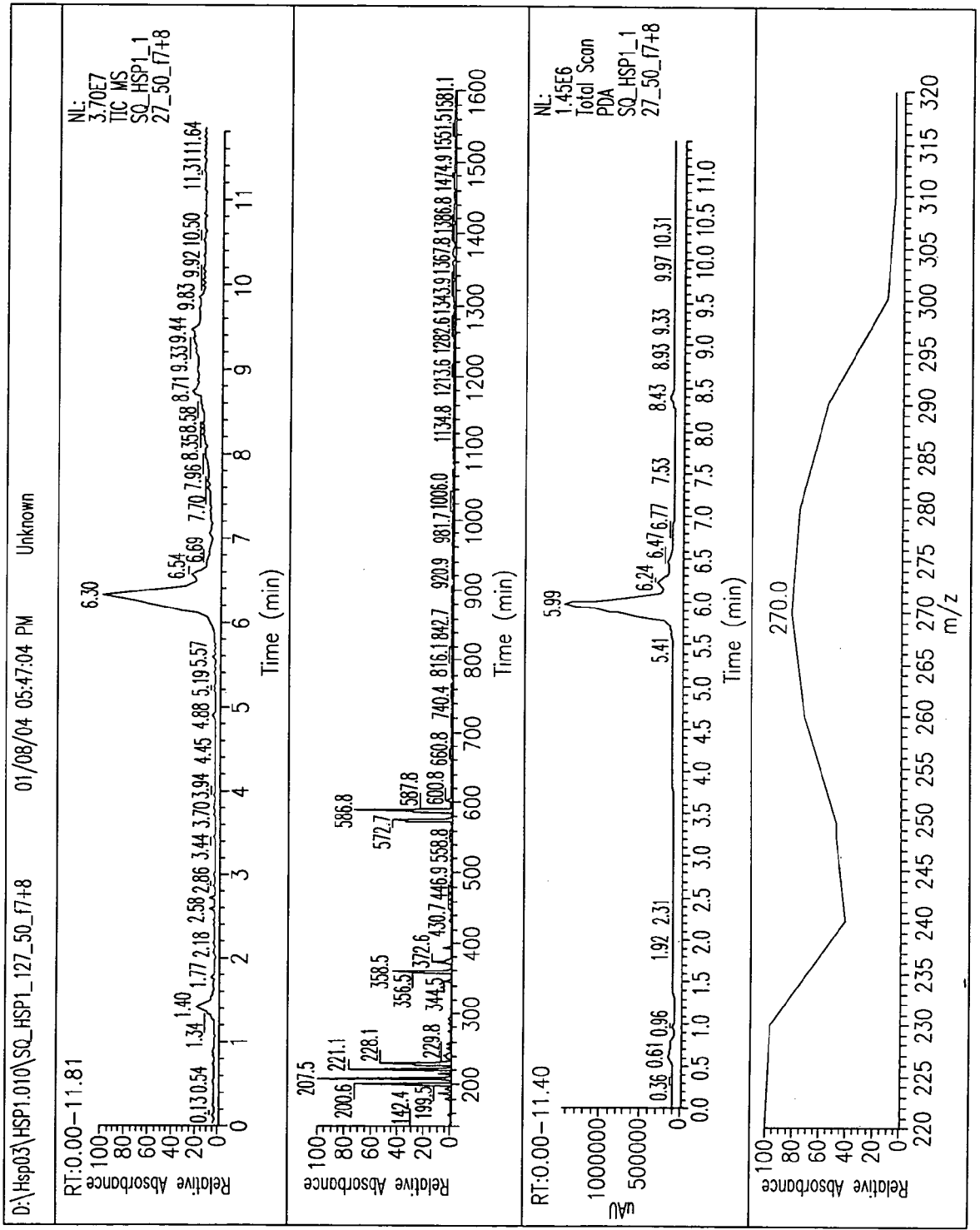

Reference to FIG. 2A and 2B shows the LC/MS analysis of MQT 1 ($C_{12}H_{29}N_5O_2$, mol.wt. 383.5) and MQT 2 ($C_{21}H_{33}N_5$, mol.wt. 355.5) respectively. The analysis involves an injected 20 µL of a 1.0 mM solution of the hydrochloride salts of MQT 1 and MQT 2 in $H_2O$ in their underivatized form. A 2.1×100 mm Waters Symmetry Shield $RP_{18}$ 3.5 µm column (Part #186000173) at 0.4 mL/min flow is used. Solvent A was $H_2O$ and Solvent B was $CH_3CN$, both with 0.05% heptafluorobutyric acid (HFBA) added as an ion-pairing reagent. A gradient elution of 5 to 90% B over 7 minutes then back to 5% over 2 minutes and finally hold at 5% for an additional 5 minutes to allow adequate re-equilibration time to starting conditions is used. Detection by ESI positive mode with a ThermoFinnigan AQA MS detector scanning the total ion current from 159 to 995 m/z range is used. UV detection by HP1100 DAD detection running from 220 to 320 nm is employed.

Cleavage of the resin following exhaustive reduction used the same general methodology as that used for the diamide compound. Despite the rather extreme methods used in the exhaustive reduction reaction moderate amounts of monoamide unreduced side-products are observed in the LC/MS analysis of the crude product. In order to completely remove this side-product, the crude product can be derivatized by $^1Boc_2O$ or heptafluorobutyric anhydrides followed by standard silica gel or fluoroflash based column chromatography. Hydrolysis of the derivatives by acid or base-mediated reactions gives the fully reduced product in monoamide-free form.

The enantiomeric form of the starting amino acids defines which of the four possible diastereiomeric forms of each compound 1 or 2 is produced. Preferably, the L version of Fmoc-1,2,3,4-tetrahydronorharman-3carboxylic acid is used. Otherwise the D-stereoversion Fmoc-D-1,2,3,4-tetrahydronorharman-3-carboxylic acid may be used. Likewise, R-Fmoc-nipecotic acid is used but the S-Fmoc-nipecotic acid may also be used.

The following non-limiting examples are presented to further illustrate the present invention.

General Chemistry Methods: The solid-phase resin Polystyrene-chlorotrityl resin with 1% DVB crosslinking has 1.49 mmole/g capacity and particle size of 100-200 mest.

The resins are dried for 4 h before the next reaction is carried out. Resin washing refers to washing for 3 minutes each three times with DMF, $^iPrOH$, THF and $CH_2Cl_2$. Loading of the resin is routinely checked by measuring the UV chromophore at 290 nm released from a measured amount of 10 mg of resin following treatment with 3mL 20% piperidine in DMF. The resulting solution is diluted 10 times in the same solvent and the absorbance at 290 nm is measured. The amount of resin loading is then calculated by the equation: Loading in mmole/g=$Abs_{290mm}$/1.65. LC/MS analysis is performed by using a 5 to 100% gradient of $H_2O$ to $CH_3CN$ both containing 0.05% heptafluorobutyric acid with a Gilson HPLC system. The gradient is over 7 min then held at 100% $CH_3CN$ for 5 min. Flow rate is 0.4 mL/min over a 2.1×100 mm Waters SymmetryShield RP18 column. Detection is by diode array detection from 210 to 410 nm and ESI MS from 100 to 1200 amu.

EXAMPLE 1

Resin 4—To 30 g (44.7 mmol) of trityl-chloride resin swelled in 300 mL of dry $CH_2Cl_2$ is added 20 mL of 1.3-aminopropanol at room temperature under a blanket of argon. The resin is gently shaken for 18 h at which time it is washed and dried. The resin is swelled in 300 mL of dry $CH_2Cl_2$ and 35.6 g (136 mmol, 3 eq) of $PPh_3$ and 200 g (136 mmol, 3 eq) of phthalimide are added at room temperature. The mixture is treated with 26.8 mL (136 mmol, 3 eq) of diisopropyldiazodicarboxylate added dropwise while gently agitating the resin. The vessel is shaken for 18 h at which time the resin is washed and dried. The resin is treated with 100 mL of hydrazine hydrate and 100 mL of absolute ethanol and then heated while shaking in a Robbins™ solid-phase synthesis oven at 65° C. The reaction is continued for 18 h and then the vessel is cooled and the resin is washed, then dried under the standard methods.

Resin 6—To 10 g (14.9 mmol) of the above resin 4 was added the solution produced by mixing 22.6 g (60 mmol, 4 eq) of HBTU, 2.0 g (14.9 mmol, 1 eq) of HOBT, 21.8 g (60 mmol, 4 eq) of (R,S)-Fmoc-nipecotic acid and 20 mL (120 mmol, 8 eq) of $^iPr_2NEt$ in 125 mL of dry DMF for 15 minutes. The resin was shaken for 4 h when it was washed and dried to give resin 5. The resin was then treated with 100 mL of 20% piperidine in DMF for 90 min when it was washed and dried to produce the product resin 6.

Resin 8—Standard coupling as the example above using Fmoc-L-1,2,3,4-tetrahydronorharman-3-carboxylic acid as the protected amino acid and 2.42 g (3.6 mmol) resin 6 is performed to gain the Fmoc protected dipeptide resin 7. This resin is deprotected under standard conditions using 20% piperidine in DMF. Washing and drying gives resin 8 than can be used directly for cleavage to diamide MQT 1, or exhaustive reduction to tetraamine MQT 2, both of which are described below.

DIAMIDE (MQT 1)—To a 600 mg portion of the above resin is added 10 mL of the cleavage cocktail of $CH_2Cl_2$/TFA/$^iPr_3SiH$ 48:48:4 at room temp. The vessel is shaken for 90 min when the solution is filtered off. The resin is washed 3 times with 10 mL each of the cleavage cocktail, $CH_2Cl_2$ and MeOH. The combined filtrate and washings are evaporated to give the crude product as a dark red oily solid in its TFA salt form. This material is purified over a 20 g column of silica gel using $CH_3CN$/cond $NH_4OH$ 80:20. Pure fractions, as confirmed by TLC in the same solvent system using ninhydrin detection, are combined and evaporated to give the pure product in its free base form. This is converted to its HCl salt form by dissolving in MeOH and treating with 3N HCl, followed by evaporation. The product obtained weighed 265 mg (65% based on 1.49 mmol/g resin substitution).

EXAMPLE 2

Exhaustive Reduction to Resin 9—To 7.5 g of the above resin 8 suspended in 50 mL of anhydrous THF is added 5 mL of trimethylborate and 5 g of anhydrous boric acid in a 300 mL round-bottomed flask with an attached reflux condenser and a magnetic stir bar. To this stirring suspension is added 50 mL of borane-dimethylsulfide complex. A large volume of hydrogen gas is evolved following this addition. The apparatus is placed under an argon atmosphere and heated to reflux. The reaction is allowed to run at this temperature for 80 h and is then allowed to cool to room temp. The contents of the flask are filtered and the filtrate is carefully quenched with MeOH and then with ice. The resin is washed 4 times each with THF, MeOH and then $CH_2Cl_2$ The resin is then suspended in 100 mL of piperidine in a 300 mL flask and this is heated to reflux for 24 h. Following cooling, the contents are washed in the standard fashion given above, and then dried under vacuum for 4 h.

TETRAAMINE (MQT 2)—To a sample 600 mg of resin 9 is added 10 mL of the cleavage cocktail ($CH_2Cl_2$/TFA/$^i$Pr$_3$SiH 48:48:4) at room temperature. The resulting suspension is shaken for 90 min. The solution is filtered off and the resin is washed 3 times each with 10 mL of the cleavage cocktail, $CH_2Cl_2$ and MeOH. The filtrate and washings are evaporated to give the crude product as a dark red oily solid in its TFA salt form. This material is purified over a 20 g column of silica gel using $CH_3CN$/cond $NH_4OH$ 80:20. Pure fractions as confirmed by TLC in the same solvent system using ninhydrin detection are combined and evaporated to give the pure product in its free base form. This is converted to its penta-HCl salt form by dissolving in MeOH and treating with 3N HCl followed by evaporation. The product contained weighs 230 mg (48% based on 1.49 mmol/g resin substitution).

Animal Tests:

EXAMPLE 3

Forced Swimming Test (Depression Test Model)—Total immobility time of rats can be assessed during a forced swimming test Porsolt, R. D., Anton, G., Blavet, N., Jalfre, M. Behavioral despair in rats, a new model sensitive to antidepressant treatments. *Eur. J Pharmacol.* 1978, 47, 379-391. A shortened immobility period reflects anti-depressant-like effects of a test compound. MQT compounds were delivered orally to rats before the swim test. The animals were observed for 6 minutes. There was a reduction in immobility at all three doses of both 1 and 2 tested (0.3, 3 and 30 mg/kg).

EXAMPLE 4

Two Compartment Light/Dark Box Test (Anxiety Test Model)—An increased amount of time in the light and an increased number of transitions between light and dark boxes during a specific time period can reflect a decrease in anxiety. Belzung, C., Misslin, R., Vogel, E., Dodd, R. H., Chapoutheir, G. Anxiogenic effects of methyl-beta-carboline-3-carboxylate in a light/dark choice situation. *Pharmacol. Biochem. Behav.* 1987, 28(1), 29-33. Both MQT compounds were delivered orally to rats before the light/dark box test. The animals were observed for 5 minutes. There was an increase in amount of time spent in the light together with an increased number of transitions between dark and light at all three doses tested (0.3, 3, and 30 mg/kg) of both drugs.

Surprisingly, the above compounds of the present invention as tested in the animal models for anxiety and depression, are active. Even more interesting is the fact that these two very hydrophilic molecules are active after being delivered via the oral administration route. Furthermore, it is interesting to note that when these compounds are tested for interaction with a wide variety of neurological receptors no clear molecular mechanism of action is apparent. Accordingly, compounds of the present invention represent a new class of hydrophilic, orally active neurological agents with an apparently undisclosed mechanism of action.

Neurological diseases treated according to the present invention include anxiety and depression.

The compounds of the present invention can be administered by any conventional means available for use in conjunction with pharmaceuticals, either as individual therapeutic agents or in a combination of therapeutic agents. They can be administered alone, but generally administered with a pharmaceutical carrier or recepient selected on the basis of the chosen route of administration and standard pharmaceutical practice.

The compounds of this invention can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 mlligrams (mg) per kilogram (kg) of body weight, with the preferred dose being 0.1 to about 30 mg/kg.

Dosage forms (compositions suitable for administration) contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment. The active ingredient can be administered employing a sustained or delayed release delivery system or an immediate release delivery system.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the, sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238-250 (1982) and *ASHP Handbook on Injectable Drugs*, Toissel, 4th ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouth washes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present invention should be sufficient to effect a therapeutic response in the animal over a reasonable time frame. One skilled in the art will recognize that dosage will depend upon a variety of factors including a condition of the animal, the body weight of the animal, as well as the condition being treated.

A suitable dose is that which will result in a concentration of the active agent in a patient which is known to effect the desired response.

The size of the dose also will be determined by the route, timing and frequency of administration as well as the existence, nature, and extent of any adverse side effects that might accompany the administration of the compound and the desired physiological effect.

Useful pharmaceutical dosage forms for administration of the compounds according to the present invention can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredients such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present invention can be administered in the form of nose drops, or metered dose and a nasal or buccal inhaler. The drug is delivered from a nasal solution as a fine mist or from a powder as an aerosol.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed as new and desired to be protected by Letters Patent of the United States is:

1. A tetrahydro-β-carboline compound represented by the following formulae:

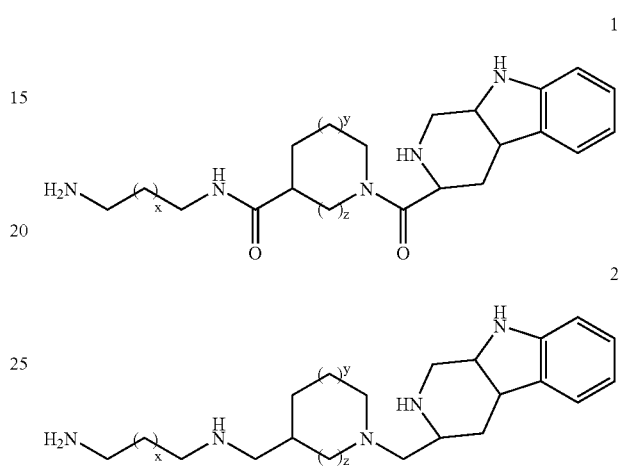

and pharmaceutically acceptable salts thereof.

2. A compound according to claim 1 being a carboline bisamide represented by formula 1.

3. A compound according to claim 1 being a carboline tetraamine represented by formula 2.

4. A compound according to claim 1 represented by the formula:

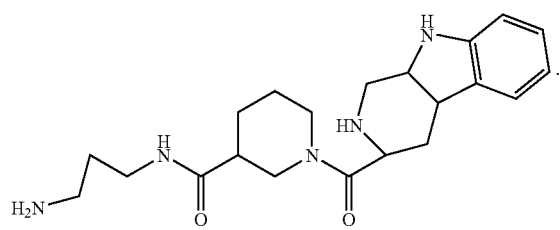

5. A compound according to claim 1 represented by the formula:

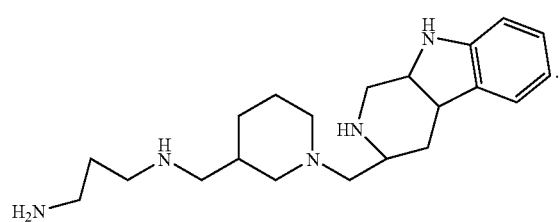

6. A pharmaceutical composition comprising a tetrahydro-β-carboline compound according to claim 1.

7. A method for treating a depression and anxiety which comprises administering to a patient suffering from a neurological disease, an effective neurological treatment amount of a tetrahydro-β-carboline compound represented by the following formulae:

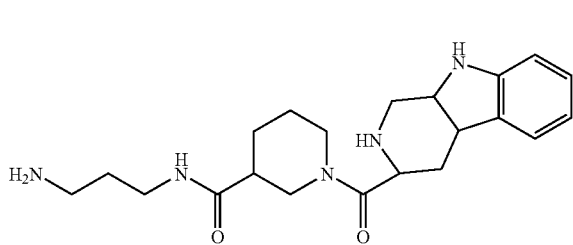

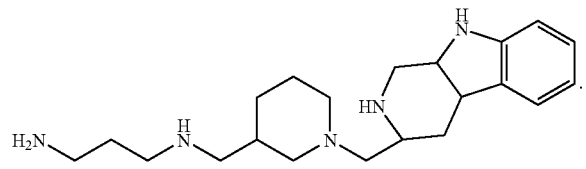

wherein x, y and z are each independently an integer of 0 to 4, pharmaceutically acceptable salts thereof.

8. The method of claim 7 wherein the neurological disease is depression.

9. The method of claim 7 wherein the neurological disease is anxiety.

10. The method of claim 7 wherein the compound is represented by the formula:

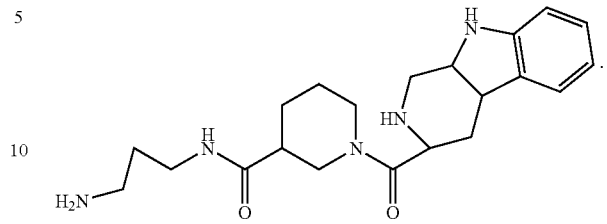

11. The method of claim 7 wherein the compound is represented by the formula:

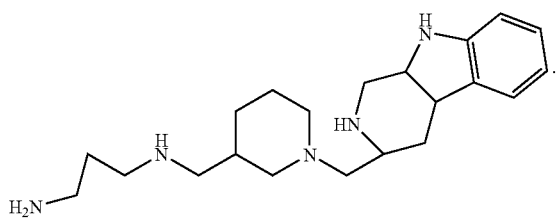

* * * * *